US007995769B2

(12) United States Patent
Nakane

(10) Patent No.: US 7,995,769 B2
(45) Date of Patent: Aug. 9, 2011

(54) SOUND CONTROL APPARATUS OF IMAGE FORMING APPARATUS

(75) Inventor: Yoshimitsu Nakane, Ryugasaki (JP)

(73) Assignee: Canon Kabushiki Kaisha (JP)

( * ) Notice: Subject to any disclaimer, the term of this patent is extended or adjusted under 35 U.S.C. 154(b) by 698 days.

(21) Appl. No.: 12/163,331

(22) Filed: Jun. 27, 2008

(65) Prior Publication Data

US 2009/0010446 A1 Jan. 8, 2009

(30) Foreign Application Priority Data

Jul. 2, 2007 (JP) ................................ 2007-173646

(51) Int. Cl.
*A61F 11/06* (2006.01)

(52) U.S. Cl. ...................................................... 381/71.1

(58) Field of Classification Search ................. 381/71.1, 381/71.3, 71.9, 71.14, 73.1; 399/1, 91, 41
See application file for complete search history.

(56) References Cited

U.S. PATENT DOCUMENTS 5,111,242 A * 5/1992 Tanimoto et al. ............. 399/167
5,289,147 A * 2/1994 Koike et al. ........................ 399/1
5,805,714 A * 9/1998 Kasama et al. .............. 381/71.8
5,930,557 A * 7/1999 Sasahara et al. ................ 399/91

FOREIGN PATENT DOCUMENTS

JP 5-119784 A 5/1993
JP 2002-311763 A 10/2002

* cited by examiner

*Primary Examiner* — Tuyen Nguyen
(74) *Attorney, Agent, or Firm* — Rossi, Kimms & McDowell LLP

(57) ABSTRACT

A sound control apparatus of image forming apparatus includes a sound-transmitting channel in which the sound in the image forming apparatus can be transmitted to the outside of the image forming apparatus, a sound-collecting portion which is provided at the sound-transmitting channel and collects sounds, and a speaker which is provided at the outside of the apparatus to the sound-collecting portion in the sound-transmitting channel and outputs sounds corresponding to the sounds collected by the sound-collecting portion, where a channel length between the sound-collecting portion and the speaker in the sound-transmitting channel is longer than a linear distance between the sound-collecting portion and the speaker.

12 Claims, 10 Drawing Sheets cross-sectional view A-A

SOUND CONTROL APPARATUS OF IMAGE FORMING APPARATUS

BACKGROUND OF THE INVENTION

1. Field of the Invention

The present invention relates to a sound control apparatus of an image forming apparatus which reduces the noise generated by image forming apparatuses such as copying machines, printers, and facsimiles.

2. Description of the Related Art

Conventionally, in image forming and reading apparatuses such as copying machines, printers, facsimiles, and scanners, a cooling fan is used to prevent the increase of temperature of the apparatuses or to discharge the ozone generated in the apparatuses out of them.

In a copying machine having a fixing device and a scanner as a high temperature generating portion in the machine, hot air from the high temperature generating portion is discharged out of the apparatus by the cooling fan provided in an opening portion of a main body. Further, an ozone exhausting fan is provided in the vicinity of a transfer portion and a separation portion in which ozone is generated in the apparatus and ozone is discharged out of the apparatus. Furthermore, a duct is disposed in order to form an exhaust channel from the high temperature generating portion or the ozone generating portion to the outside of the apparatus.

However, the cooling fan and the ozone exhausting fan are placed in the vicinity of the surface of the copying machine body. Thus, noise during operation of the cooling fan and the ozone exhausting fan is directly emitted from the apparatus to the outside, which may cause discomfort to the person near the apparatus body.

The condition in a plurality of the high temperature generating portions is not always uniform. Further, an exhaust passage of an exhaust duct for each high temperature generating portion is not necessarily formed into an uniform shape in view of restrictions of the shape of the copying machine body. Therefore, difference in the cooling efficiency in each of the high temperature generating portions is caused. It is necessary to determine the amount of air in the cooling fan based on the point of measurement which shows the highest temperature in the apparatus. For this reason, some of the high temperature generating portions are overly cooled, which causes the increase of noise in the cooling fan. The same problem is caused in the ozone exhausting fan.

In order to prevent noises of the cooling fan and the ozone exhausting fan, a structure in which sounds (driving sound etc.) in the apparatus are transmitted to the outside of the apparatus via the exhaust duct is proposed. In the structure, a technique that the sounds in the exhaust duct are reduced by detecting the sounds in the exhaust duct and outputting sounds in opposite phase to the sounds into the exhaust duct (active noise control) is used. When the active noise control (hereinafter referred to as ANC) is used, sounds of the cooling fan and the ozone exhausting fan can be reduced in the duct. As a result, sounds emitted from the copying machine to the outside can be reduced (see Japanese Patent Application Laid-Open (JP-A) No. 2002-311763).

The structure in which sounds in the image forming apparatus (driving sound etc.) are transmitted to the outside of the apparatus via the exhaust duct has been exemplary described. Needless to say, when the inside and outside of the image forming apparatus are communicated, the sounds in the apparatus can be transmitted to the outside.

Here, in the ANC, it is necessary that arithmetic processing of the detected sounds is performed by a digital signal processor (hereafter referred to as DSP), the sounds in opposite phase are calculated and output into the exhaust duct by the speaker. Thus, the following problems have been caused.

It is necessary to make a distance between the position which detects sounds in the duct and the position of the speaker which outputs sounds in opposite phase longer. For example, the time for arithmetic processing is 1 ms, the processing time for converting the sounds into a digital sound when taking an analog sound into the DSP is 0.5 ms, and the processing time for converting the sounds into an analog sound in order to output the digital sound of the DSP to the speaker is 0.5 ms. In that case, it is necessary that the total time from when sounds are detected till when they are output by the speaker is at least 2 ms. On the other hand, the sound speed in a temperature of 25° C. is about $346\times10^3$ (mm/s) and thus it is necessary that the channel from when sounds are detected till when they are output by the speaker is about $346\times10^3$ (mm/s)$\times$0.002 (s)=692 mm.

In the case where the channel length between the sound detecting position and the output position of the speaker is shorter than 692 mm, sounds in opposite phase cannot be outputted from the speaker till when the detected sounds reach the speaker. Thus, it is difficult to reduce the detected sounds. In the structure in which the channel length between the sound detecting position and the output position of the speaker is shorter, it is necessary to use a high-speed and expensive arithmetical element when sounds are reduced.

In order to solve the above-described problems, a method for lengthening a duct channel is considered. However, when the duct channel is lengthened, the size of the copying machine body is disadvantageously increased.

A sound absorbing apparatus having a duct is formed with a first straight path which is continuous with a fan and a second straight path which is continuous with the first straight path via a refracting portion is described in JP-A No. 05-119784. A microphone for detection is provided at the first straight path and a speaker is disposed so as to release a reversal sound out of the second straight path. In JP-A No. 05-119784, the microphone for detection and the speaker are provided in the first straight path. Therefore, in the case of the structure described in JP-A No. 05-119784, when a distance from the microphone for detection to the speaker is ensured to effectively reduce sound by the ANC, the length of the duct from the microphone for detection to the speaker is lengthened and thus the size of an apparatus is increased.

SUMMARY OF THE INVENTION

The present invention provides the sound control apparatus of the image forming apparatus which can reduce noise without increasing the size of the image forming apparatus body.

The present invention provides a sound control apparatus of image forming apparatus comprising: a sound-transmitting channel in which the sound in the image forming apparatus can be transmitted to the outside of the image forming apparatus; a sound-collecting portion which is provided at the sound-transmitting channel and collects sounds; and a speaker which is provided at the outside of the apparatus to the sound-collecting portion in the sound-transmitting channel and outputs sounds corresponding to the sounds collected by the sound-collecting portion; wherein a channel length between the sound-collecting portion and the speaker in the sound-transmitting channel is longer than a linear distance between the sound-collecting portion and the speaker. According to the present invention, the noise can be reduced without increasing the size of the apparatus body.

Further features of the present invention will become apparent from the following description of exemplary embodiments with reference to the attached drawings.

DESCRIPTION OF THE EMBODIMENTS

First Embodiment

The first embodiment of the sound control apparatus of the image forming apparatus according to the present invention will be described with reference to the drawings.

(Image Forming Apparatus 1)

Figure 1:
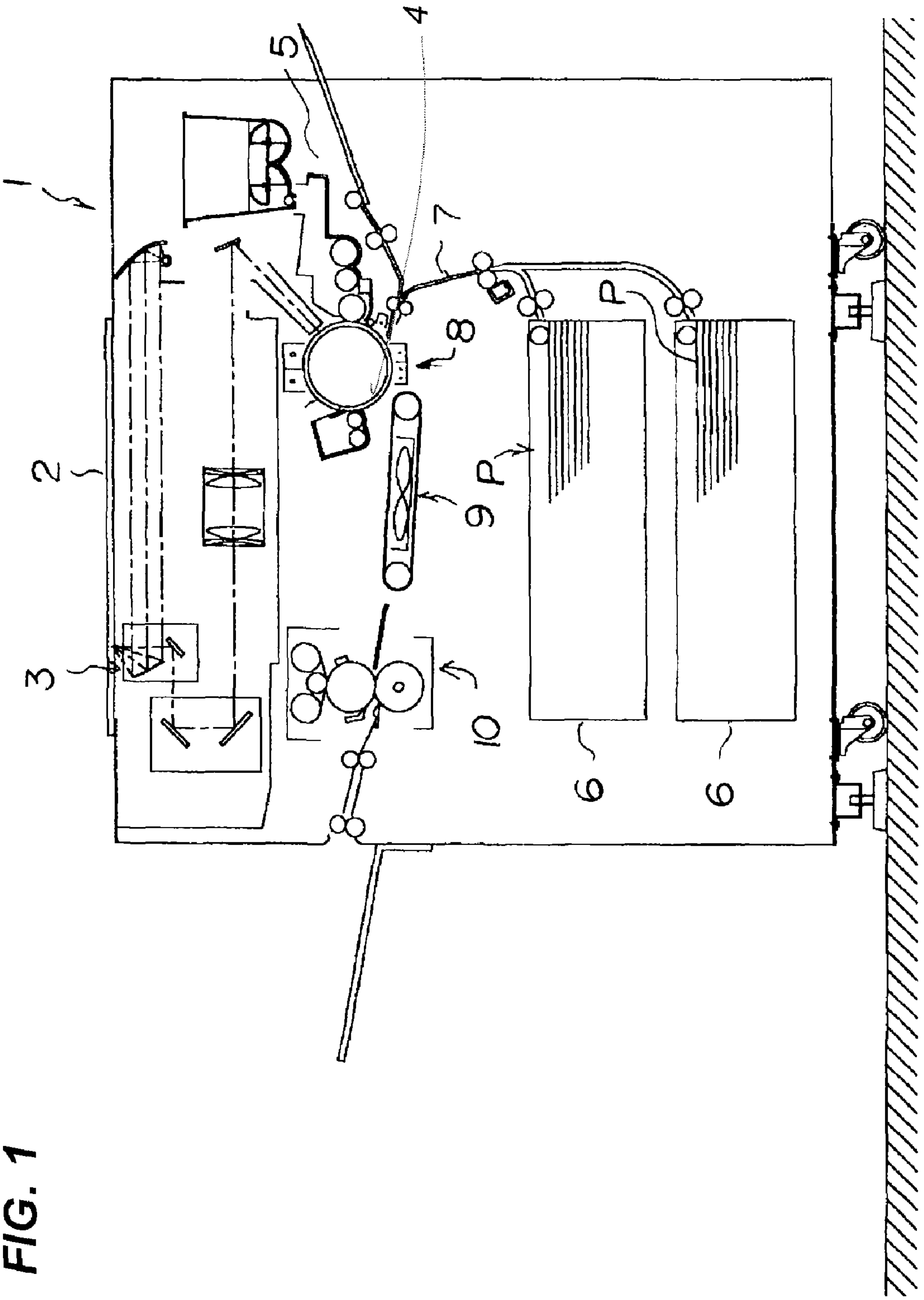
FIG. 1 is a cross-sectional view illustrating an image forming apparatus in which a sound control apparatus according to a first embodiment is mounted.

FIG. 1 is a cross-sectional view illustrating an image forming apparatus 1 in which the sound control apparatus according to the first embodiment is mounted. An original is disposed and pressed down by a pressure plate 2 and then is illuminated with light. The reflected light from the original is brought to a photoconductor drum 4. A latent image is formed on the photoconductor drum 4. A toner image of the latent image is formed by a developing portion 5. A transfer material P disposed in a cassette 6 is conveyed to a transfer and separation portion 8 via a conveying path 7. The toner image is transferred to the transfer material P by the transfer and separation portion 8. The transfer material P to which the toner image is transferred is conveyed to a fixing apparatus 10 by a conveying portion 9. After fixing the toner image, the transfer material P is discharged out of the image forming apparatus 1.

The image forming apparatus 1 has the sound control apparatus including the airflow system and the ANC system 17.

(Airflow System)

Figure 2:
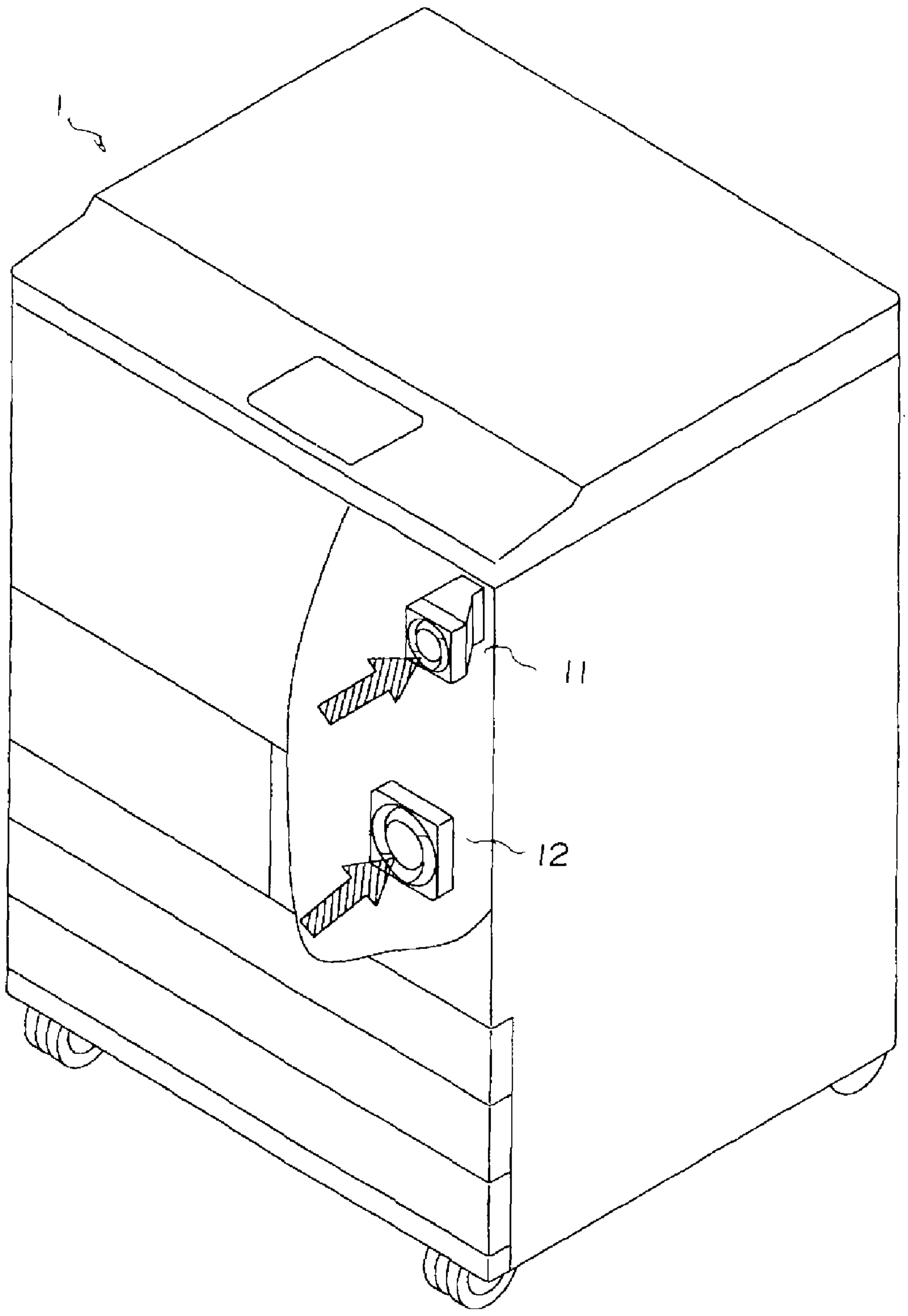
FIG. 2 is a perspective view of the image forming apparatus which illustrates an airflow system.
Figure 3:
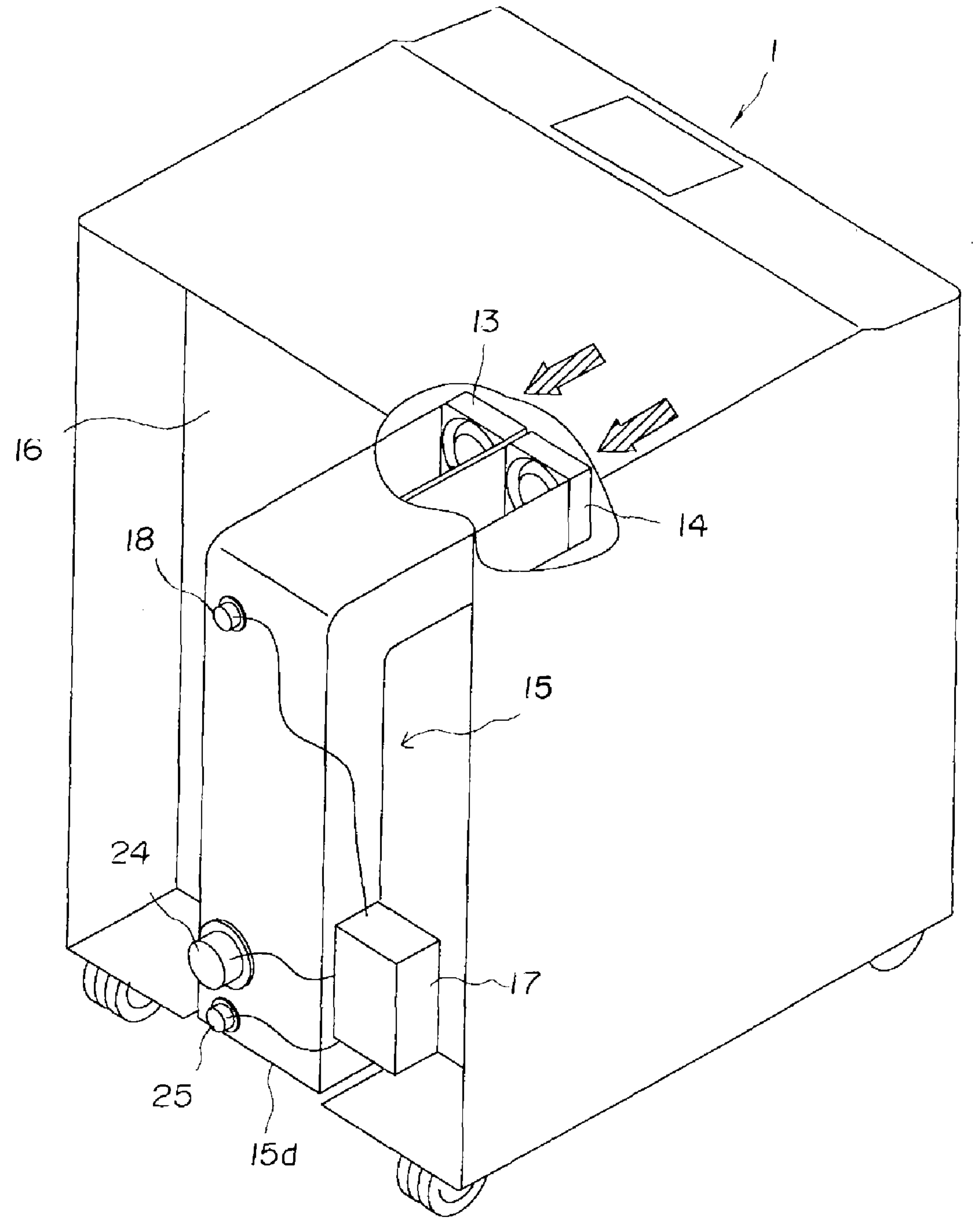
FIG. 3 is a perspective view of the image forming apparatus which illustrates the airflow system.

FIGS. 2 and 3 are perspective views of the image forming apparatus which illustrates the airflow system. As shown in FIGS. 2 and 3, the airflow system of the image forming apparatus 1 includes suction fans 11 and 12, an ozone exhausting fan 13 which exhausts ozone, a fixed heat-exhausting fan 14, and the exhaust duct 15.

The suction fans 11 and 12 are disposed in the upper part and on the front surface of the image forming apparatus 1.

The ozone exhausting fan 13 has a role in discharging the ozone generated in the image forming apparatus 1 out of the image forming apparatus 1 through an ozone decomposing filter (not shown).

The fixed heat-exhausting fan 14 plays a role in discharging the heat surrounding the fixing apparatus 10 out of the image forming apparatus 1 and reducing the internal temperature. In this regard, the ozone exhausting fan 13 also exhausts the air in the image forming apparatus 1. Thus, the heat in the image forming apparatus 1 is also exhausted.

The exhaust duct 15 is mounted on a rear side plate 16 of the image forming apparatus 1. The ozone exhausting fan 13 and the fixed heat-exhausting fan 14 are provided at the inlet of the exhaust duct 15. An opening portion (outlet) 15*d* of the exhaust duct 15 is disposed at the rear and undersurface of the image forming apparatus 1.

As shown in FIG. 2, the air is sucked into the image forming apparatus 1 by the suction fans 11 and 12. As shown in FIG. 3, the sucked air is discharged from the opening portion 15*d* to the outside of the image forming apparatus 1 by the ozone exhausting fan 13 and the fixed heat-exhausting fan 14 through the exhaust duct 15.

There is a source of heat and ozone between the suction fans 11 and 12 and the exhausting fans 13 and 14. Therefore, the heat and ozone being generated in the image forming apparatus 1 is discharged out of the image forming apparatus 1 by the airflow system.

Figure 4A:
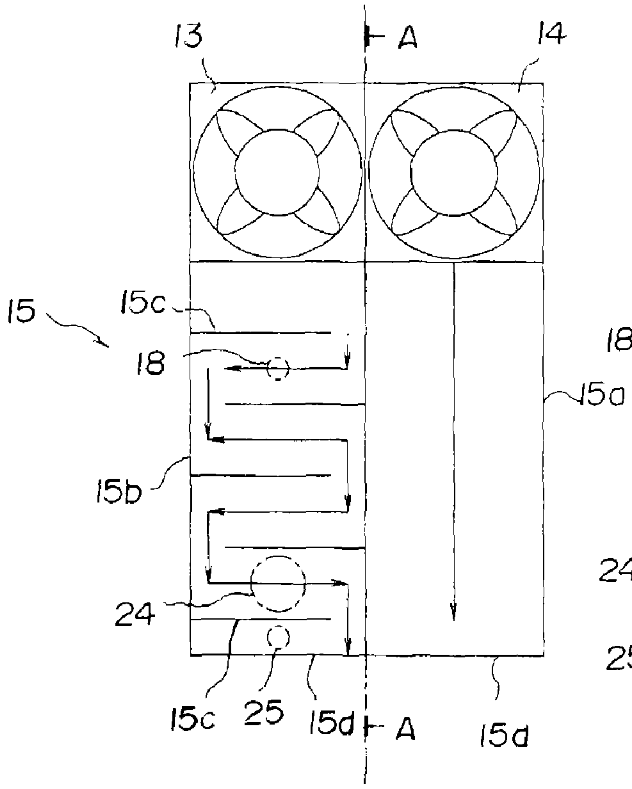
FIG. 4A is a cross-sectional view illustrating the inside of an exhaust duct 15.
Figure 4B:
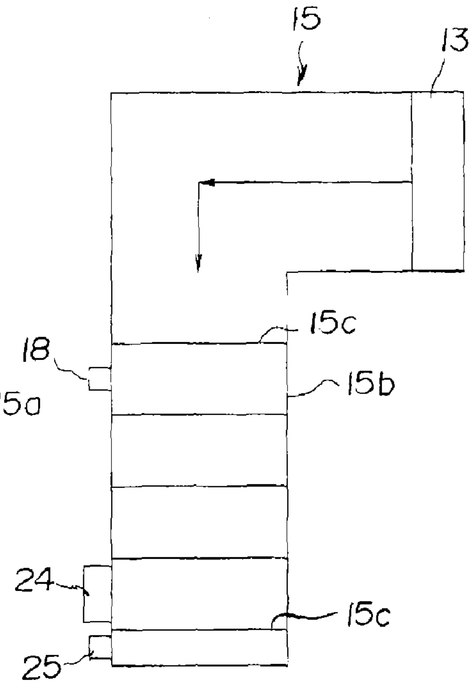
FIG. 4B is a cross-sectional view A-A of FIG. 4A.

FIG. 4A is a cross-sectional view illustrating the inside of the exhaust duct 15. FIG. 4B is a cross-sectional view A-A of FIG. 4A.

As shown in FIG. 4, the exhaust duct 15 has two channels of a first duct 15*a* and a second duct 15*b*. The first duct 15*a* has a straight shape (straight-line channel) which is formed at a linear distance from the fixed heat-exhausting fan 14 to the opening portion 15*d*. The second duct 15*b* has a zigzag shape which is formed by projecting partition plates 15*c* alternately from right and left side faces of the second duct 15*b* between the ozone exhausting fan 13 and the opening portion 15*d*.

The exhaust duct 15 is a sound-transmitting channel in which the noise in the image forming apparatus can be transmitted to the outside of the image forming apparatus. The second duct 15*b* of the exhaust duct 15 has a shape which satisfies the relation of $L \geqq S \times T$. In the equation, L is the length of a channel from a control microphone 18 to a secondary sound source speaker 24, T is the time from when the sounds (noises) is collected by the control microphone 18 till when the sound is outputted by the secondary sound source speaker 24, and S is the sound speed. Here, the channel length of the second duct 15*b* of the exhaust duct 15 is longer than the linear distance between the inlet and the outlet which are connected by the partition plates 15*c*.

The air flown into the exhaust duct 15 by the fixed heat-exhausting fan 14 is passed through the first duct 15*a* and the air is exhausted from the opening portion 15*d*.

The channel of the air flown into the exhaust duct 15 by the ozone exhausting fan 13 is changed in the direction of arrow by the partition plates 15*c* disposed in the second duct 15*b* and the air is finally discharged from the opening portion 15*d*.

Usable examples of the material of the exhaust duct 15 include resins such as ABS resins. It is necessary to set the thickness of the exhaust duct 15 to the level (for example, at least 5 mm) in which the vibration of the fixed heat-exhausting fan 14 and the ozone exhausting fan 13 are not transmitted.

A sound-absorbing material (absorbing unit, not shown) which absorbs sounds is disposed in the exhaust duct 15 (the first duct 15*a* and the second duct 15*b*) reduces the sounds passing through the inside of the exhaust duct 15. The sound-absorbing material is effective in reducing a high frequency sound with a frequency of 2 kHz or more.

(ANC System 17)

The ANC system (active sound reduction system) 17 is disposed in the second duct 15*b*. The ANC system 17 absorbs noises such as the sound generated from the ozone exhausting fan 13 and the driving sound generated in the image forming apparatus 1 which are emitted from the second duct 15*b* to the outside of the image forming apparatus 1.

Figure 5:
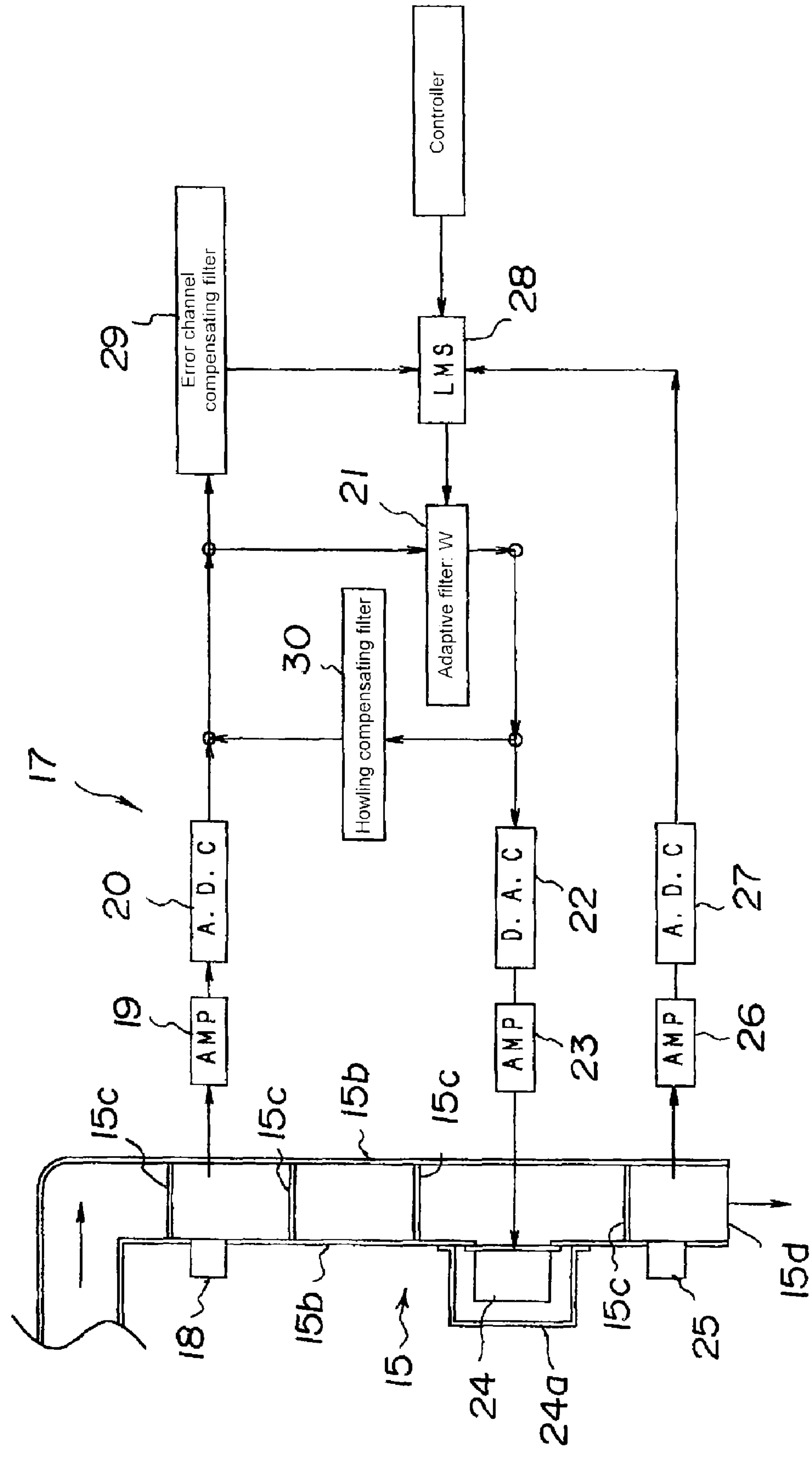
FIG. 5 is a cross-sectional view of the exhaust duct and an electric block diagram of an ANC system.

FIG. 5 is a cross-sectional view of the exhaust duct 15 and an electric block diagram of the ANC system 17. As shown in FIG. 5, the ANC system 17 has the control microphone 18, a voltage amplifier 19, an AD converter 20, an adaptive filter 21, a DA converter 22, a voltage amplifier 23, the secondary sound source speaker 24, and an error microphone 25.

The control microphone 18 is a sound-collecting portion which collects sounds and is provided at the inlet of the second duct 15*b* of the exhaust duct 15. The control microphone 18 is disposed so that the surface which detects sounds of the control microphone 18 is parallel to the inner wall surface of the second duct 15*b*.

The secondary sound source speaker 24 which is provided at the outlet of the second duct 15*b* of the exhaust duct 15 outputs sounds in opposite phase to noises. A speaker cover 24*a* is provided surrounding the secondary sound source speaker 24. The speaker cover 24*a* is formed so that the output of the secondary sound source speaker 24 is directed to the second duct 15*b*.

The error microphone 25 is a detection unit which detects sounds and is present in the image forming apparatus, provided at the external side than the secondary sound source speaker 24 in the sound-transmitting channel. The error microphone 25 is disposed so that the inner wall surface of the second duct 15*b* faces the surface which detects sounds.

Here, the control microphone 18 is provided at the inlet side of the second duct 15*b* and the secondary sound source speaker 24 is provided at the outlet side of the second duct 15*b*. The second duct 15*b* has a zigzag shape which is formed by projecting partition plates 15*c* alternately from right and left side faces of the second duct 15*b*. Therefore, the length of the sound-transmitting channel from the control microphone 18 to the secondary sound source speaker 24 is longer than the linear distance between the control microphone 18 and the secondary sound source speaker 24 because of the zigzag shape of the second duct 15*b*.

The length of the sound-transmitting channel from the control microphone 18 to the secondary sound source speaker 24 is lengthened by the partition plates 15*c* and thus the relation of $L \geqq S \times T$ is easily satisfied even when the high-speed and expensive arithmetical element is not used.

The operation of the ANC system 17 will be described. First, sounds of the inside second duct 15*b* is detected by the control microphone 18. The sounds are amplified by the voltage amplifier (AMP) 19. The amplified sounds are converted to a digital signal by the AD converter (A.D.C) 20. Then, the phase of the signal is reversed by the adaptive filter: W (21), which is converted to an analog signal by the DA converter (D.A.C) 22 to produce a sound. Then, the sound is amplified by the AMP 23. The amplified sounds are added into the second duct 15*b* by the secondary sound source speaker 24. The secondary sound source speaker 24 generates sounds corresponding to the sounds collected sound by the control microphone 18.

Namely, sounds in opposite phase to the sound detected by the control microphone 18 are emitted into the second duct 15*b* by the secondary sound source speaker 24 and the sounds in the second duct 15*b* are canceled by sound interference.

The sounds (sounds in opposite phase to noises) emitted from the secondary sound source speaker 24 are overlapped with the original sound (noise) and detected by the error microphone 25. The sounds detected by the error microphone 25 are amplified by an AMP26. Thereafter, the amplified sounds are converted to a digital signal by an AD converter (A.D.C) 27 and then entered into an LMS arithmetic operation portion 28.

In the LMS arithmetic operation portion 28, arithmetic processing is performed so as to minimize the sounds detected by the error microphone 25, the result is input into the adaptive filter: W (21), and the sounds emitted from the secondary sound source speaker 24 are determined. That is, feedback control is performed so as to minimize the sound detected by the error microphone 25.

An error channel compensating filter: C (29) has a characteristic of the transmission from the secondary sound source speaker 24 to the error microphone 25. In order to synchronize the timing of the detected signals of the control microphone 18 with the timing of the detected signals of the error microphone 25, arithmetic processing is performed in the LMS arithmetic operation portion 28 and the error channel compensating filter 29 adjusts the sounds emitted from the secondary sound source speaker 24.

The channel shown in a howling compensating filter 30 is a channel that the sounds from the secondary sound source speaker 24 are fed back to the control microphone 18, which causes howling. Thus, the howling compensating filter 30 is disposed in order to prevent the howling.

Figure 6:
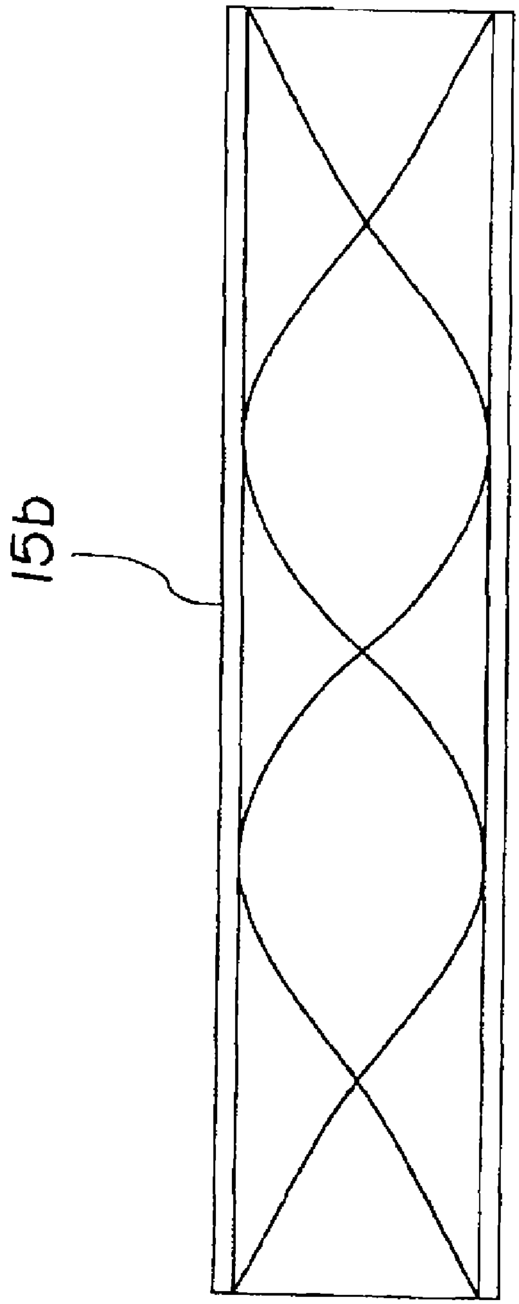
FIG. 6 is a schematic view of an acoustic mode which schematically illustrates a sound pressure level of the inside of the duct.

Subsequently, the position of the control microphone 18 will be described. It is preferable that the control microphone 18 is disposed in the portion where the sound pressure is high in the second duct 15*b*. FIG. 6 is a schematic view of the acoustic mode which schematically illustrates the sound pressure level of the inside of the duct. As shown in FIG. 6, the sound pressure level in the second duct 15*b* varies depending on location. The sound pressure level in the protruding portion becomes larger while the sound pressure level in the joint portion becomes smaller. The acoustic mode changes depending on the sound frequency. In that case, it may be considered that the acoustic mode is formed by the overall sound pressure level, for example, in the range of 500 Hz to 3000 Hz.

Figure 7:
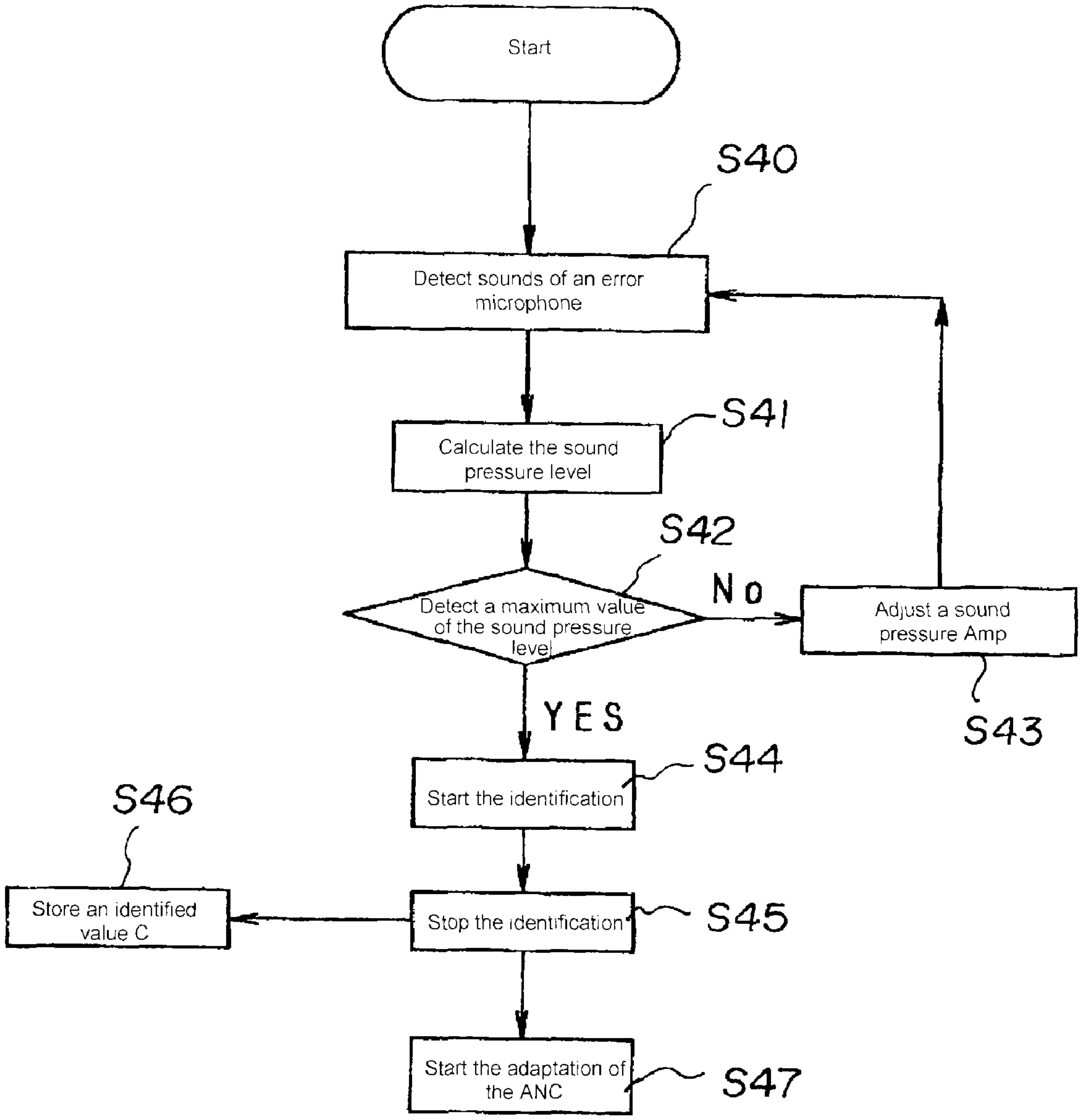
FIG. 7 is a systematic flow chart illustrating an operation procedure of an ANC system 17 in the first embodiment.

Subsequently, the flow of a sound reduction by the ANC system 17 will be described. FIG. 7 is a flowchart at the time of sound reduction in the ANC system 17.

As shown in FIG. 7, the sounds in the second duct 15*b* are first detected by the control microphone (C microphone) 18 and the error microphone (E microphone) 25 (S40). At the time, the obtained sounds are subjected to the fast Fourier Transform algorithm (hereafter referred to as FFT) and the sound pressure level is calculated (S41).

Next, the detection of a maximum value of the sound pressure level obtained by the control microphone 18 and the error microphone 25 at the current level of the AMPs 19 and 26 is determined (S42).

When it is not detected, the AMP19 and the AMP26 are adjusted so as to be detected and the flow is returned to the step S40 (S43).

When it is detected, the sound including all sounds in the entire frequency band (so-called white noise) is outputted by the secondary sound source speaker 24 and the AMP23 of the secondary sound source speaker 24 is adjusted so as to capture a maximum value of the sounds detected by the error microphone 25 in an appropriate position. In the state, the white noise is outputted from the secondary sound source speaker 24 (identification initiation, S44).

At the end of the identification process, an identified value C is input to the error channel compensating filter 29 (S45) and stored (S46). After the operation, the adaptation of the ANC system 17 is started (S47).

In the channel in the second duct 15*b* the distance between the control microphone 18 and the error microphone 25 needs to be 692 mm or more. 692 mm=the sound speed (about $346\times10^3$ (mm/s))×the time from when the error microphone 25 detects the sound to when the speaker 24 output the sound.

It is preferable that a distance between the secondary sound source speaker 24 and the error microphone 25 is shorter. However, when the distance is too short, howling is easily generated between the secondary sound source speaker 24 and the error microphone 25. For that reason, the center of the secondary sound source speaker 24 is separated from the center of the error microphone 25 at a distance of about 70 mm.

(Results of Sound-Reduction)

Figure 8:
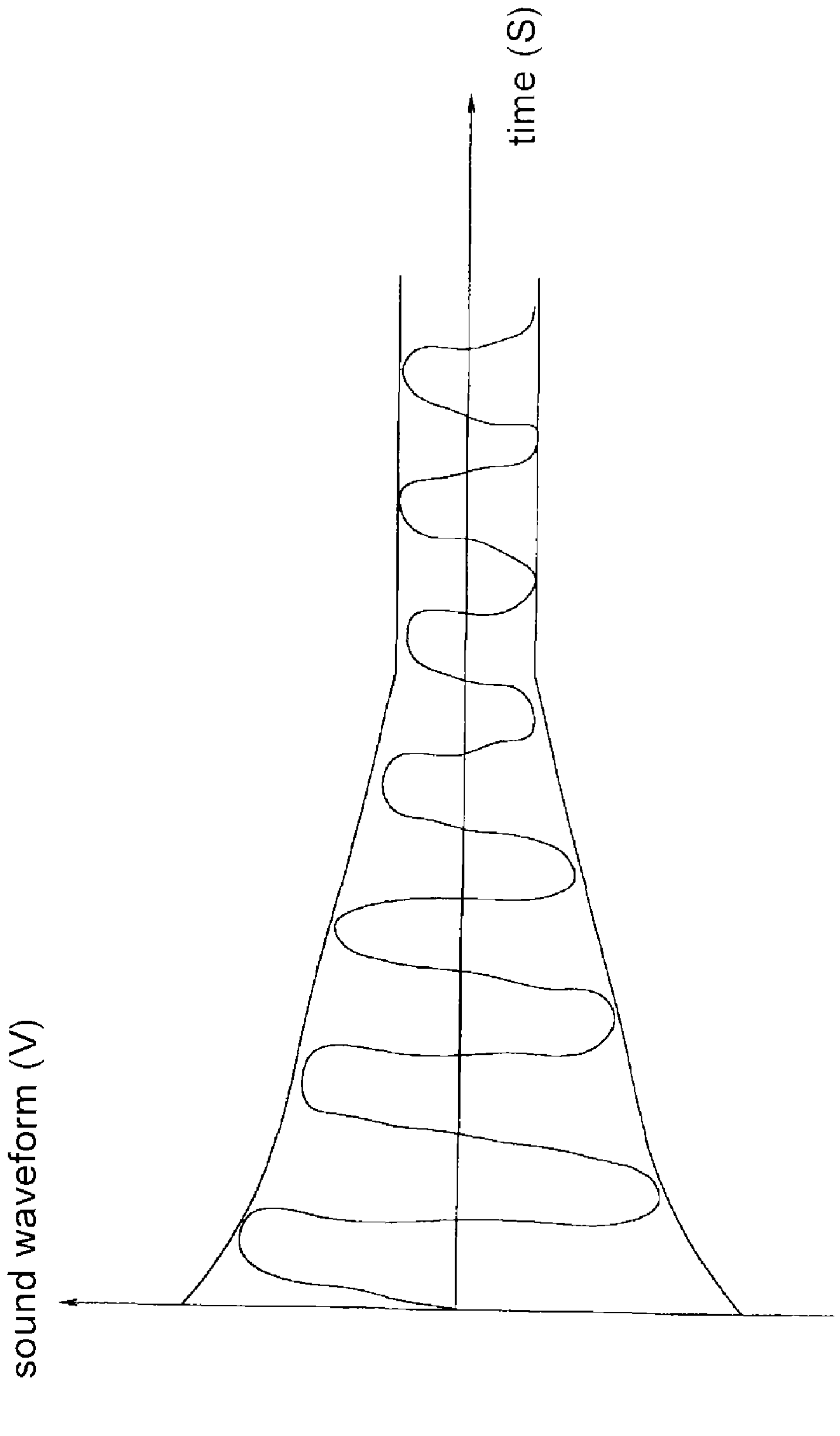
FIG. 8 illustrates a sound waveform when sounds of the inside of the exhaust duct are detected in the first embodiment.
Figure 9:
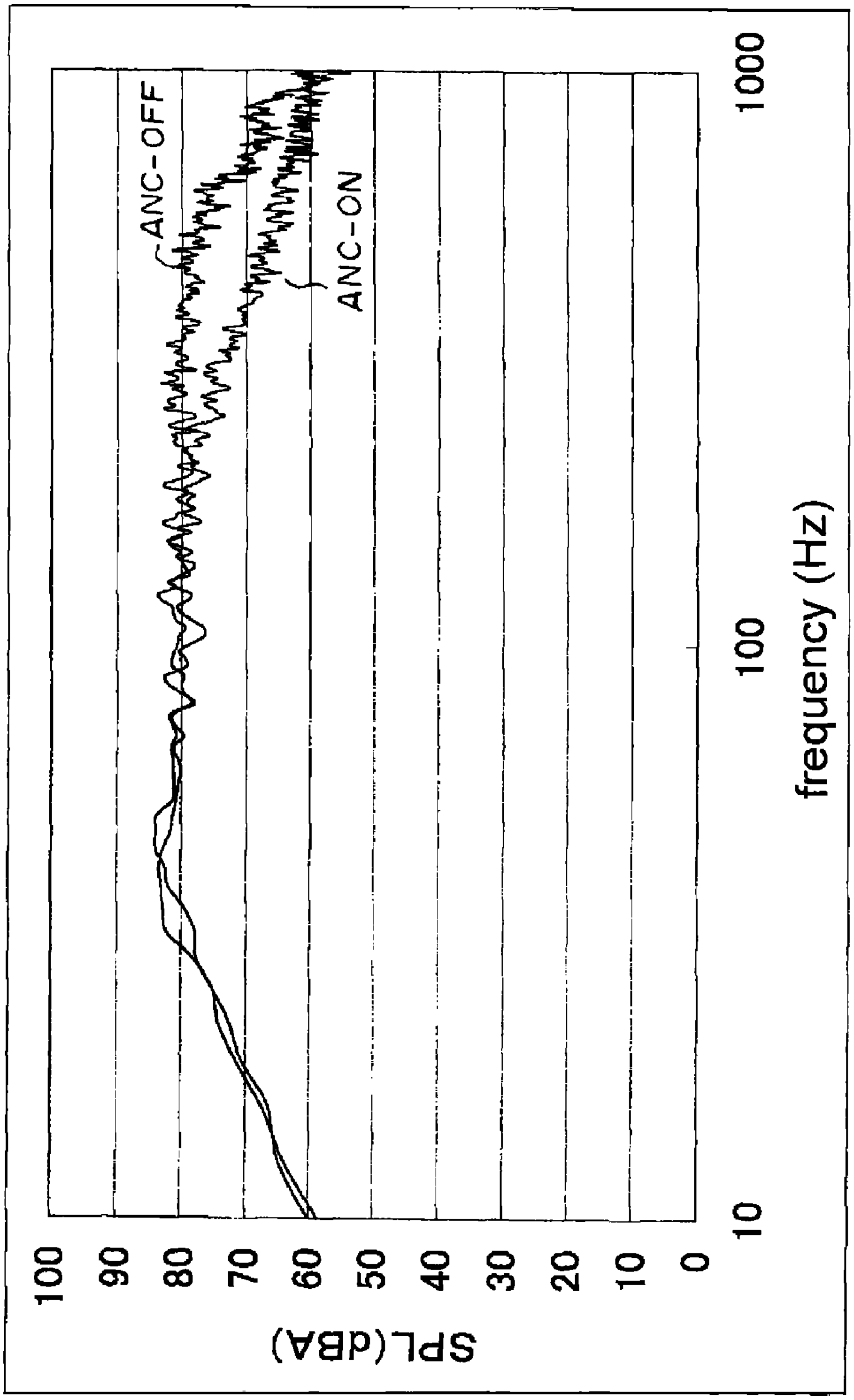
FIG. 9 is a graph illustrating the results during either operation or non-operation of the ANC when sounds of the inside of the exhaust duct are FFT-processed in the first embodiment.

FIGS. 8 and 9 illustrate results of sound-reduction which is obtained by operating the ANC system 17. In FIG. 8, a time (S) is illustrated on the horizontal axis and a sound waveform (V) is illustrated on the vertical axis. The sound waveform is a voltage waveform detected by the error microphone 25. FIG. 9 is a graph with a frequency (Hz) on the horizontal axis and a sound pressure level SPL (dBA) on the vertical axis when the sound waveform in FIG. 8 is FFT-processed.

As shown in FIG. 8, when the ANC system 17 is operated, the sound waveform (V) becomes smaller over time. Further, a sound reduction effect (maximum level; 10 dBA in the range of 10 to 1000 Hz) can be obtained as shown in FIG. 9.

According to the embodiment, the channel of the ANC system 17 is ensured without increasing the size of the exhaust duct 15. Therefore, the ANC system 17 is applied without increasing the size of the image forming apparatus 1, which allows for reducing the sounds (noises) of the fixed heat-exhausting fan (cooling fan) 14 and the ozone exhausting fan 13 which are emitted out of the apparatus through the exhaust duct 15. Consequently, the silence (sound-reduction) in using the image forming apparatus 1 can be achieved.

The length of the channel to which the ANC system 17 is applied can be lengthened and thus an effect of the ANC system 17 can be largely exerted.

A low frequency sound can be reduced by the ANC system 17 and a high frequency sound can be reduced by the sound-absorbing material. Thus, the sound reduction can be achieved efficiently and a power saving effect is provided.

Since a high frequency noise can be reduced, the image forming apparatus 1 which enables a quiet office environment to be maintained and has few complaints from the user can be provided.

The exhaust duct 15 is divided into two channels (the first duct 15*a* and the second duct 15*b*). One channel (the second duct 15*b*) is a sound-absorbing channel which reduces sound and the other channel is an exhaust channel which does not absorb sound but just exhausts air. The balance between the sound absorbing efficiency and the exhaust efficiency can be achieved by using such a structure.

Second Embodiment

Next, the second embodiment of the sound control apparatus of the image forming apparatus according to the present invention will be described with reference to the drawings. The same numeral references are applied to the overlapped parts in the first embodiment and the description will not be repeated here.

Figure 10:
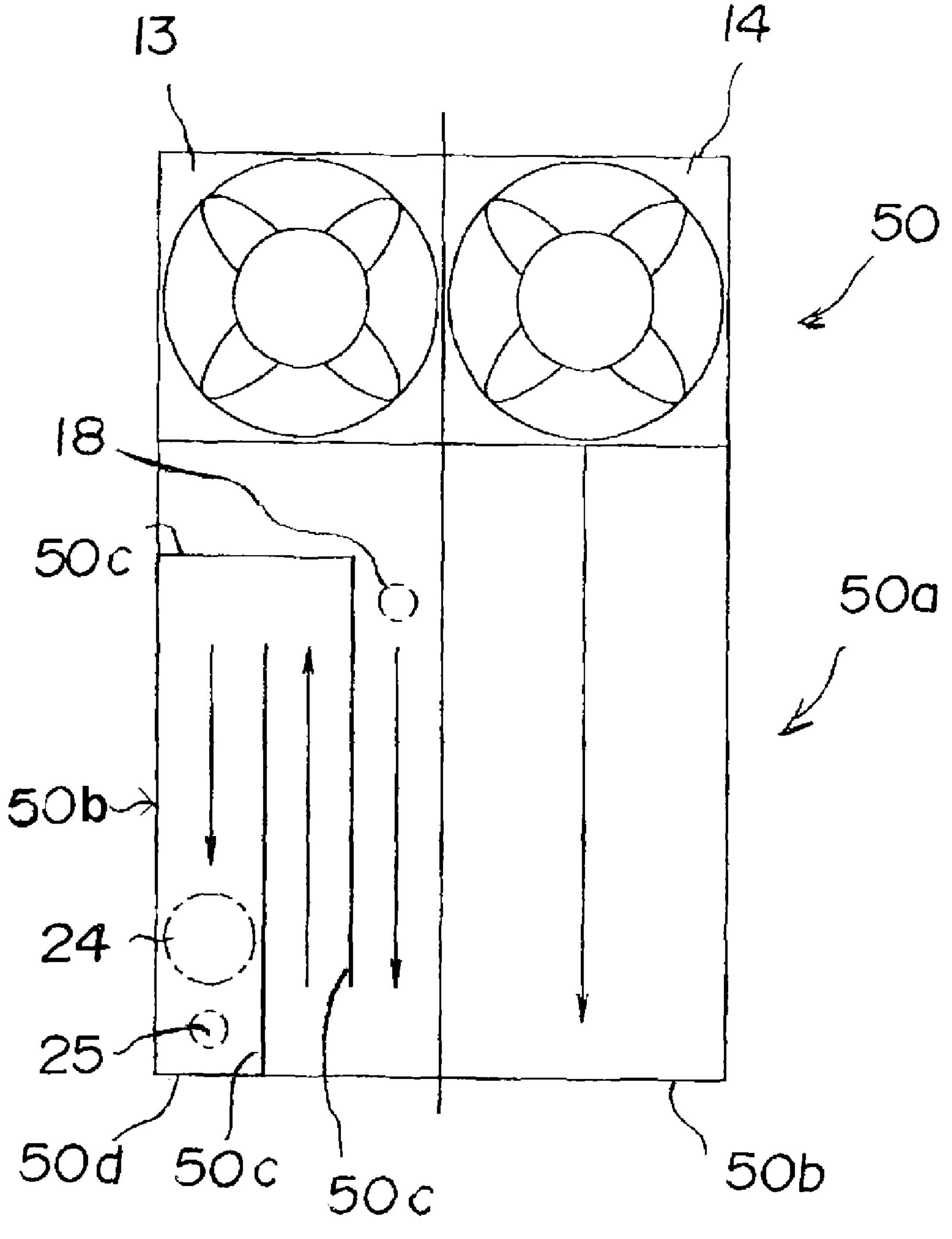
FIG. 10 is a cross-sectional view of the inside of the exhaust duct in the second embodiment.

FIG. 10 is a cross-sectional view illustrating the exhaust duct 50 according to the second embodiment. As shown in FIG. 10, in the sound control apparatus of the embodiment, the exhaust duct 15 of the sound control apparatus of the first embodiment is changed to the exhaust duct 50.

In the exhaust duct 50, the disposition of the partition plates 15*c* of the first embodiment is changed and the flow of air is changed from a horizontal direction to a vertical direction.

The exhaust duct 50 has two channels of ducts 50*a* and 50*b*. The first duct 50*a* has a straight shape (straight-line channel) which is formed at a linear distance from the fixed heat-exhausting fan 14 to the opening portion 50*d*. The second duct 50*b* has a zigzag shape which is formed by projecting partition plates 50*c* alternately above and below in the gap between the ozone exhausting fan 13 and the opening portion 50*d*.

The air flown into the exhaust duct 50 by the fixed heat-exhausting fan 14 is passed through the first duct 50*a* and the air is exhausted from the opening portion 50*d*.

The channel of the air flown into the exhaust duct 50 by the ozone exhausting fan 13 is changed in the direction of arrow by the partition plates 50*c* disposed in the second duct 50*b* and the air is finally discharged from the opening portion 50*d*.

Usable examples of the material of the exhaust duct 50 include resins such as ABS resins. It is necessary to set the thickness of the exhaust duct 50 to the level (for example, at least 5 mm) in which the vibration of the fixed heat-exhausting fan 14 and the ozone exhausting fan 13 are not transmitted.

A sound-absorbing material (not shown) which absorbs sounds is disposed in the exhaust duct 50 (ducts 50*a* and 50*b*) absorbs the sounds passing through the inside of the exhaust duct 50. The sound-absorbing material is effective in absorbing a high frequency sound with a frequency of 2 kHz or more.

In addition, the shape of the exhaust duct is not limited to the zigzag shape in the first and second embodiments. Any shape may be used as long as the relation of $L \geqq S\times T$ is satisfied. For example, the shape from the inlet to the outlet may be spiral (swirl).

In any of the embodiments, the image forming apparatus which transfers the image in which the latent image is formed on the photoconductor drum 4 and developed to a transfer paper has been exemplified. However, the image forming apparatus is not limited thereto. The examples thereof may include an image forming apparatus which transfers the image from the photoconductor drum to the transfer paper through an intermediate transfer member and an image forming apparatus which forms the image on paper by an inkjet method.

Further, the ducts which exhaust heat and air out of the image forming apparatus have been exemplified as the sound-transmitting channels, but not limited thereto. A duct which takes air into the image forming apparatus can also be applied to the sound control apparatus. The sound-transmitting channel is not limited to a duct which allows air to enter and exit. Any image forming apparatus portion which allows the inside of the apparatus to be communicated with the outside thereof can be applied to the sound control apparatus.

While the present invention has been described with reference to exemplary embodiments, and it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-173646, filed Jul. 2, 2007, which is hereby incorporated by reference herein in its entirety.

What is claimed is:

1. A sound control apparatus of image forming apparatus comprising:

a sound-transmitting channel in which the sound in the image forming apparatus can be transmitted to the outside of the image forming apparatus;

a sound-collecting portion which is provided at the sound-transmitting channel and collects sounds; and a speaker which is provided at the outside of the apparatus to the sound-collecting portion in the sound-transmitting channel and outputs sounds corresponding to the sounds collected by the sound-collecting portion;

wherein a channel length between the sound-collecting portion and the speaker in the sound-transmitting channel is longer than a linear distance between the sound-collecting portion and the speaker.

2. The sound control apparatus of image forming apparatus according to claim 1, the sound control apparatus has a configuration so that the channel length between the sound-collecting portion and the speaker in the sound-transmitting channel is longer than the linear distance between the sound-collecting portion and the speaker; and when the channel length between the sound-collecting portion and the speaker in the sound-transmitting channel is L, a time from when the sounds are collected by the sound-collecting portion till when the sounds are outputted by the speaker is T, and a sound speed is S, the relation of $L \geqq S \times T$ is satisfied.

3. The sound control apparatus of image forming apparatus according to claim 1, wherein a shape between the sound-collecting portion and the speaker in the sound-transmitting channel is zigzag or spiral.

4. The sound control apparatus of image forming apparatus according to claim 1 comprising:

a detection unit which is present in the apparatus, provided at the external side than the speaker in the sound-transmitting channel and detects sounds;

wherein the speaker generates sounds corresponding to sounds detected by the detection unit.

5. The sound control apparatus of image forming apparatus according to claim 1, wherein the sound-transmitting channel has two channels, one channel of the two channels is a straight channel which is formed at a linear distance from a sound source to an outlet of the sound-transmitting channel, and the other channel is a channel having the sound-collecting portion and the speaker.

6. The sound control apparatus of image forming apparatus according to claim 1, wherein the sound-transmitting channel has a plurality of partition plates so that the length of a sound-transmitting channel between the sound-collecting portion and the speaker in the sound-transmitting channel is lengthened.

7. The sound control apparatus of image forming apparatus according to claim 1, wherein the speaker outputs sounds in opposite phase to the sound collected by the sound-collecting portion.

8. An image forming apparatus comprising:

a channel to connect an inside of an image forming apparatus body to outside air;

a sound-collecting portion which collects sounds at a first position in the channel; and a speaker which outputs sounds corresponding to the sounds collected by the sound-collecting portion at a second position in the channel, wherein the second position is nearer to the outside air than the first position;

wherein a channel length of between the first position and the second position in the channel is longer than a linear distance between the first position and the second position.

9. An image forming apparatus according to claim 8, when the channel length between the first position and the second position in the channel is L, a time from when the sounds are collected by the sound-collecting portion till when the sounds are outputted by the speaker is T, and a sound speed is S, the relation of $L \geqq S \times T$ is satisfied.

10. An image forming apparatus according to claim 8, wherein a shape between the sound-collecting portion and the speaker in the sound-transmitting channel is zigzag or spiral.

11. An image forming apparatus according to claim 8, wherein the channel has a plurality of partition plates so that the length of the channel between the first position and the second position in the channel is lengthened.

12. An image forming apparatus according to claim 8, wherein the speaker outputs sounds in opposite phase to the sound collected by the sound-collecting portion.

* * * * *